United States Patent [19]

Kinney et al.

[11] Patent Number: 5,083,865
[45] Date of Patent: Jan. 28, 1992

[54] PARTICLE MONITOR SYSTEM AND METHOD

[75] Inventors: Patrick Kinney, Sunnyvale; Boris Fishkin; Jun Zhao, both of San Jose; Anand Gupta, Santa Clara; Robert Bendler, Mountain View, all of Calif.

[73] Assignee: Applied Materials, Inc., Santa Clara, Calif.

[21] Appl. No.: 522,606

[22] Filed: May 11, 1990

[51] Int. Cl.$^5$ .............................. G01N 21/00
[52] U.S. Cl. .............................. 356/338; 356/339; 359/509; 359/512
[58] Field of Search .............................. 356/335–343, 356/440; 350/584, 588

[56] References Cited

U.S. PATENT DOCUMENTS

| | | | |
|---|---|---|---|
| 3,495,259 | 2/1970 | Rocholl et al. | 350/588 |
| 3,696,230 | 10/1972 | Friedrich | 350/584 |
| 3,861,198 | 1/1975 | Shea | 350/584 |
| 4,343,552 | 8/1982 | Blades | 350/584 |
| 4,443,072 | 4/1984 | Ballard | 350/584 |
| 4,738,528 | 4/1988 | Craft | 350/584 |
| 4,786,188 | 11/1988 | Myhre et al. | 350/584 |
| 4,836,689 | 6/1989 | O'Brien et al. | 350/584 |
| 4,886,356 | 12/1989 | Paradis | 356/440 |

Primary Examiner—Richard A. Rosenberger
Assistant Examiner—Hoa Pham
Attorney, Agent, or Firm—Philip A. Dalton

[57] ABSTRACT

A particle monitor for a processing chamber exhaust line is disclosed which incorporates exhaust line heating, purge gas flow over surfaces such as optical windows in the exhaust gas line, and a thermally and electrically insulating particle monitor mounting arrangement. The features collectively protect the particle monitor from electrical disturbance and from the heated inlet and maintain the optical surfaces clean and free of depositions from the exhaust gas flow for an extended period. The arrangement also suppresses etching of the optical surfaces.

13 Claims, 2 Drawing Sheets

PARTICLE MONITOR SYSTEM AND METHOD

FIELD OF THE INVENTION

The present invention relates to particle monitors such as those used in semiconductor processing reactors.

BACKGROUND OF THE INVENTION

State-of-the-art semiconductor deposition reactors may incorporate laser-based optical systems for monitoring the particulate levels in the exhaust gas flow. However, such particle monitors are interactive with the gas flows which they monitor in that various reaction byproducts, non-reacted species, etc., deposit on and etch and, thus, optically degrade surfaces which come in contact with the gas flow. For example, deposition on the particle monitor lenses and other surfaces in and around the associated laser beam scatter laser light into the collection optics, causing noise in the photodiode or other detector. As a consequence, the reactor must be taken out of service frequently, so that surfaces such as particle monitor windows can be cleaned or replaced.

SUMMARY OF THE INVENTION

Objects

In view of the above discussion, it is a primary object of the present invention to provide a particle monitoring system and method characterized by decreased susceptibility to damage and degradation by the gases which are being monitored.

It is another object to provide a particle monitor and associated method of operation which suppress deposition on particle monitor surfaces including lenses and other optical windows associated with the particle monitor and thus decrease associated light scattering and noise.

It is a related object to provide a particle monitor system and associated method of operation which reduce noise caused by stray electrical currents in the exhaust line.

It is a related object to provide a particle monitor system and method for increasing the number of semiconductor wafers which can be processed before maintenance and/or cleaning of the particle monitor surfaces such as lenses/windows is necessary.

Summary

In one aspect, a particle monitoring system which embodies our invention and achieves the above and other objectives comprises means for directing a beam of light into a gas-containing region such as the exhaust line of a semiconductor processing reactor; optical detector means for monitoring particles illuminated by the beam of light; optical windows such as lenses or separate windows through which said light means and said detector means communicate into the region; and means for heating the region proximate the optical windows for suppressing deposition on the windows. The particle monitoring system may comprise means for flowing purge gas across at least the optical access window associated with the detector means, to provide a gas barrier between the detector window and the monitored gases. Also, the system may comprise a barrier window between the optical access window and the monitored gases. Preferably, the monitor system includes means for attaching the monitor to the exhaust line, i.e., for inserting the monitor into the gas line, with electrical and thermal separation from the gas line.

In another aspect, our invention relates to a method for monitoring particles in the exhaust line of a workpiece processing reactor using optical monitoring components mounted to the exhaust line, and comprises: operating the particle monitoring system components to detect particles in the gas line while heating the gas line in the vicinity of the particle monitoring components to suppress deposition from the exhaust gases on the surfaces of particle monitoring system components exposed to the exhaust line gases.

In addition, the method further comprises flowing purge gas over said surfaces of the particle monitoring system components.

BRIEF DESCRIPTION OF THE DRAWINGS

The above and other aspects of our present invention are described with respect to the drawings in which.

DETAILED DESCRIPTION OF THE PREFERRED EMBODIMENT

Figure 1:
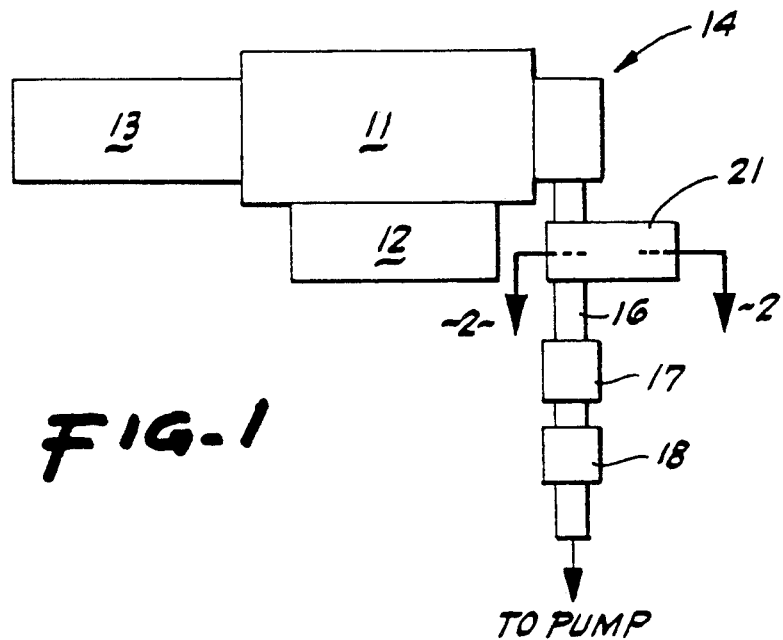
FIG. 1 schematically depicts a CVD processing chamber which incorporates a particle monitor in the exhaust line.

FIG. 1 schematically depicts a deposition system which incorporates a particle monitor, the precision CVD 5000 system available from Applied Materials, Inc., 3050 Bowers Avenue, Santa Clara, Calif. 95054. This state-of-the-art system is described in detail in commonly assigned U.S. Pat. No. 4,872,947, entitled "CVD of Silicon Oxide Using TEOS Decomposition and In-Situ Planarization Process", issued Oct. 10, 1989, in the name of inventors Wang et al. The illustrated CVD reactor system incorporates a vacuum chamber 11 which is heated by a lamp module 12. Wafers are supplied to and removed from the chamber via a vacuum loadlock chamber 13.

The exhaust system 14 is located on the opposite side of the chamber from the loadlock and comprises an exhaust line 16; associated isolation valve 17; throttle valve 18; a vacuum pump system; and a particle monitor system which includes monitor 21 and associated computer or controller (not shown) and which benefits from being constructed and from operating in accordance with our invention.

Figure 2:
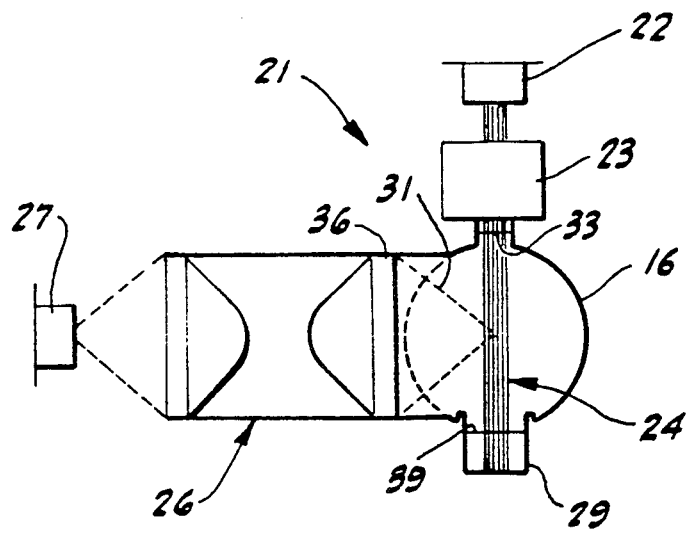
FIG. 2 is a schematic cross-sectional view taken along line 2—2 in FIG. 1 depicting components of the particle monitoring system and their relationship to the exhaust gas line.

FIG. 2 is a diametrical cross-section through the exhaust line 16 schematically illustrating the relationship of the components of the particle monitor 21 of FIG. 1 to the exhaust line 16. A high intensity laser beam 24 is generated by a laser diode 22 and focused by associated shaping optics 23 through window 33 into the interior of the exhaust line 16. Light trap 29 absorbs the laser beam 24 after it traverses through the line 16. When a particle in the exhaust line passes through the high intensity beam 24, the laser beam 24 is scattered, as indicated at 31, and the scattered light is collected by optical collection system 26 and directed to photodiode sensor 27. The electronics associated with the sensor amplify the electrical output pulse from the sensor for processing by the system software.

As alluded to above, each of the three external systems or elements of the monitor, (1) the laser diode 22 and focusing optics 23; (2) the collection optics 26 and photodiode 27; and (3) the light trap 29, communicate optically with the chamber via respective surfaces such as optical component lenses or other surfaces or separate windows, such as (1) 33; (2) 36; and (3) 39.

According to our present invention, the objectives of decreasing the deposition on surfaces in a gas line, such as the optically transparent surfaces through which an optical particle monitor interfaces with the interior of the gas line, and thereby decreasing noise resulting from scattering of the laser light, are achieved by heating the line and gas upstream of the surface. In addition or separately, the surfaces are protected by flowing purge gas over the surfaces and/or by interposing a protective window between the optical surface and the exhaust gases. Also, the mounting arrangement isolates the monitor from the exhaust line both electrically and thermally.

Figure 3:
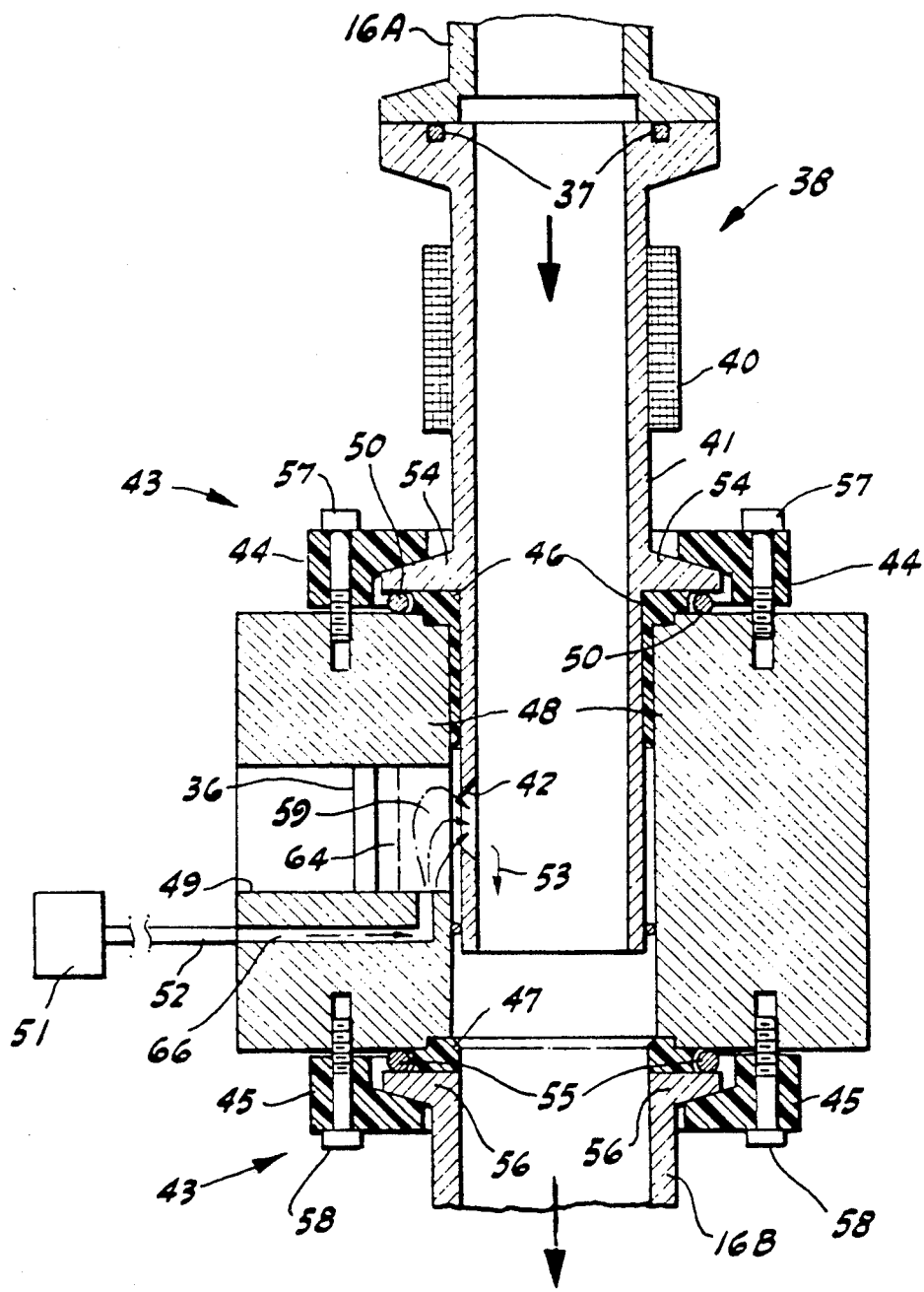
FIG. 3 schematically depicts a particle monitor which embodies the features of our present invention, including the arrangement by which the monitor is mounted to and interfaces with an associated exhaust line.

FIG. 3 schematically depicts the exhaust gas line 16 and its unique interface with the optical monitoring system, which suppress deposition on and etching of exposed gas line surfaces. First, a heated gas line insert 38 is inserted into the gas line 16. The insert 38 mates at one end with an inlet gas line section 16A from the chamber and at the opposite end with an outlet gas line section 16B which is connected to the valve(s) and vacuum pump(s). The insert line 38 comprises a heat conducting pipe section 41, of material such as aluminum, which is sealed to the gas line section 16A via face-sealing O-rings 48. The line 38 is heated by an electrical resistance coil 40 or other suitable arrangement, and extends into the particle monitor to heat the exhaust gas directly upstream of the optical surfaces. For standard CVD processing, the element 40 is used to heat pipe section 41 to about 125° C. and to heat the exhaust gases. This temperature suppresses the cold wall effect and the resulting deposition of process reaction products on the particle monitoring optics as well as on other surfaces exposed to the gases in the exhaust line. As shown, preferably the thermally conductive line 38 extends into the monitor, past the optical windows, so that the exhaust gases are heated until they exit the monitor. As discussed elsewhere, the particle monitor is thermally isolated from the heater to prevent damage. However, the optical surfaces and other surfaces are heated slightly, to about 50° C., and this slightly elevated temperature may also reduce deposition.

Secondly, isolation clamp assembly 43 seals the insert line 41 to the output exhaust line 16B and thermally and electrically insulates the monitor 21 from the exhaust line. The assembly 43 comprises a block 48 which is joined to the insert line 41 at one end and to the exhaust line section 16B at the other. The monitoring optics are mounted to the block 48. Referring also to FIG. 2, the laser beam 24 propagated by laser diode 22 and laser shaping optics 23 is directed into the interior of the exhaust gas line 16 through optically transparent window 33. Similarly, the light trap 29 communicates with the interior of the gas line via a light trap surface which is illustrated schematically at 39. The particle sensing access provided by the photodiode and the collection optics 26 is via aperture 49 in block 48 and associated lens 36 of the collector optics.

Cooperating annular plastic clamp 44, intermediately positioned O-ring 50 and plastic O-ring centering ring 46 (which is fitted between the line 41 and the block 48) engage the flange 54 on line section 41 and are cinched together by the bolts 57—57. During assembly, the O-ring 50 is seated in an annular groove in the periphery of the centering ring 46. As a result, when the bolts 57 are tightened to secure the clamp 44 and block 48 against the flange 54, the O-ring 50 is automatically positioned and compressed between the block 48 and flange 54, providing a vacuum-tight seal. Similarly, at the outlet end of the particle monitor block 48, O-ring 55 is positioned on centering ring 47 between associated annular plastic clamp 45 and the mounting block 48, which are secured to outlet side flange 56 by bolts 58—58. The O-ring 55 is compressed between the block 48 and flange 56, thereby providing a vacuum-tight seal to the line 16B. The cooperating plastic clamp 44 and O-ring centering ring 46, and plastic clamp 45 and O-ring centering ring 47 thermally and electrically isolate the particle monitor from the heated inlet and the gas line and thereby prevent thermally-induced damage and thermal and electrical interference with the operation of the sensitive particle monitor. For example, noise caused by stray electrical currents through the exhaust line is suppressed by the plastic fittings.

In summary, the fittings of plastic or materials of similar qualities provide vacuum sealed assembly of the gas line insert 41, gas line 16 and particle monitor 21; prevent stray electrical currents from passing through the particle monitor; and thermally isolate the particle monitor from the heated inlet.

Thirdly, deposition and etching of the internal exhaust line surfaces such as the optical surfaces such as lenses and other surfaces which serve as windows are suppressed by flowing purge gas over the surfaces. For example, as shown in FIG. 3, gas from a source 51 flows via line 52 through bore 66 in the particle monitor block 48, out an aperture in front of the lens 36, over the lens and then into a small chamber 59 defined between the lens and the gas line insert 41, then via insert line aperture 42 into the exhaust line. The small volume of the chamber 59 helps to establish a positive pressure differential between the chamber and the gas line which enhances the separation provided by the purge gas flow. That is, the purge gas barrier is provided in part by the gas flow across the optical window and in part by the slightly higher pressure in the chamber relative to the exhaust gas line.

Fourth, and referring specifically to FIG. 3, chemical attack on the surfaces such as the monitor lens 36 can be eliminated by mounting optically transparent protective windows such as window 64 (shown in phantom in FIG. 3) on the interior (exhaust line) side of the optical surfaces. The protective windows block etching and allow cleaning of the particle monitor using standard acidic solutions used to clean deposits in process chambers. Also, windows of different material can be used for different processes and gases, for example, quartz windows for epitaxial reactors and sapphire windows for chemical vapor deposition reactors which use fluorine etchants.

To date, the use of the heated insert 38 to heat the exhaust gas flow to about 125° C. has extended the period between cleaning and/or maintenance from about 20 wafer process cycles to more than 200 wafer process cycles, an improvement of one order of magnitude. It is anticipated that the other improvements lead to additional substantial increases in the number of process cycles between maintenance or cleaning. In particular, present results indicate the use of the purge gas increases the between-maintenance interval by several orders of magnitude.

What is claimed is:

1. A particle monitoring system for monitoring particles in a gas flowing through an exhaust line comprising: means for directing a beam of light into a gas-containing region of an exhaust gas line of a workpiece processing reactor, for illuminating particles in gas flowing through the exhaust line; optical detector means for monitoring particles in the gas illuminated by the beam of light; optically transparent windows in the exhaust line for providing optical access for said light means and said detector means into the gas-containing region; and means for heating the gas-containing region proximate the optical windows for suppressing deposition of particulates from the monitored gas on the windows.

2. The particle monitoring system of claim 1, further comprising means for flowing purge gas across at least the optically transparent window associated with the detector means for providing gas separation between the window and the monitored gas.

3. The particle monitoring system of claim 1, further comprising means for flowing purge gas across the windows for providing gas separation between the windows and the monitored gas.

4. The particle monitoring system of claim 1, further comprising a second window interposed between at least one of the optically transparent windows and the monitored gas.

5. The particle monitoring system of claim 4, further comprising means for flowing purge gas across the second window.

6. A particle monitoring system comprising: means for directing a beam of light into an exhaust gas line of a workpiece processing reactor; optical detector means for monitoring particles illuminated by the beam of light; optically transparent windows in the exhaust gas line for providing optical access for said light means and said detector means into the exhaust line; means for heating the exhaust line proximate the optical windows for suppressing particulate deposition on the windows; and means mounting the light beam directing means and the detector means to the exhaust line, said mounting means being adapted for thermally and electrically insulating the light beam directing means and the detector means from the exhaust line.

7. The particle monitoring system of claim 6, wherein particle monitoring system components comprising the light beam directing means and the detector means are mounted on a thermally-conductive section of the exhaust line which extends from the upstream side of the components to the downstream side thereof; and wherein the means for heating the exhaust line is mounted in the thermally-conductive section.

8. The particle monitoring system of claim 6, wherein the exhaust line includes a thermally-conductive section; wherein the means for mounting particle monitoring system components including the light beam directing means and the detector means to the exhaust line comprises: a mounting block mounting particle said monitoring system components thereto; a pair of flanges formed about the exhaust line proximate opposite ends of the mounting block; a pair of inserts adapted for insertion between the mounting block and the exhaust line, said inserts mating with the flanges and the mounting block and being adapted for mounting sealing O-rings; mounting rings mating with the flanges on the opposite side thereof from the O-ring-mounting inserts; and means for cooperatively clamping the mounting rings and the O-ring-mounting inserts to the flanges; and wherein at least selected ones of the mounting rings, the O-ring-mounting inserts and the mounting block are formed of thermally and electrically insulating material for insulating the particle monitoring system components from the exhaust line.

9. The particle monitoring system of claim 8, wherein the exhaust line section extends from a point upstream of the particle monitoring system components to the downstream side of the components and wherein the means for heating the exhaust line is a heating coil mounted on the exhaust line section.

10. A method for monitoring particles in gas in the exhaust line of a workpiece processing reactor using optical monitoring means mounted in the exhaust line, the optical monitoring means having surfaces exposed to the gas in the gas line, comprising: operating the particle monitoring means to detect particles in the exhaust line while heating the exhaust line in the vicinity of the particle monitoring means to suppress particulate deposition from the exhaust gases on the surfaces of the particle monitoring means exposed to the exhaust line gases.

11. The method of claim 10, further comprising flowing purge gas over said surfaces of the particle monitoring system components.

12. The method of claim 10, further comprising providing an optically transparent window between the particle monitoring means and the exhaust line gases, for isolating the component from the exhaust gases.

13. The method of claim 12, further comprising flowing purge gas over the window on the side thereof exposed to the exhaust gases.

* * * * *